United States Patent [19]

Grasso

[11] Patent Number: 4,537,988

[45] Date of Patent: Aug. 27, 1985

[54] PROCESS FOR THE PREPARATION OF 2-(4-HYDROXYPHENYL)-3-METHYL-BUTYRIC ACID

[75] Inventor: Charles P. Grasso, Princeton, N.J.

[73] Assignee: American Cyanamid Company, Stamford, Conn.

[21] Appl. No.: 501,337

[22] Filed: Jun. 6, 1983

[51] Int. Cl.³ .............................................. C07C 65/01
[52] U.S. Cl. ...................................... 562/478; 560/75
[58] Field of Search ........................... 562/478; 560/75

[56] References Cited

FOREIGN PATENT DOCUMENTS 7185234 11/1982 Japan ................................... 562/478
7203030 12/1982 Japan ................................... 562/478
2083023  3/1982 United Kingdom ................ 562/478

Primary Examiner—Paul J. Killos
Attorney, Agent, or Firm—H. G. Jackson

[57] ABSTRACT

An integrated process for the preparation of 2-(4-hydroxyphenyl)-3-methylbutyric acid from the corresponding 2-(4-chlorophenyl)-3-methylbutyronitrile through hydrolysis of the nitrile by strong base to the corresponding carboxylic acid followed by formation of the corresponding phenol by nucleophilic displacement of the chlorine with a strong base in the presence of copper salts, and if so desired metallic copper, is described.

2 Claims, No Drawings

PROCESS FOR THE PREPARATION OF 2-(4-HYDROXYPHENYL)-3-METHYLBUTYRIC ACID

The invention herein described relates to a process for the preparation of 2-(4-hydroxyphenyl)-3-methylbutyric acid of structural formula (I)

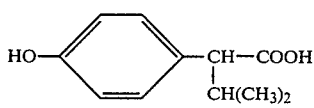

The above acid is a valuable intermediate for the preparation of pyrethroid insecticides in general and in particular the pyrethroid of structural formula (II)

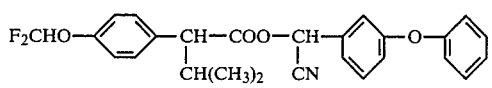

The pyrethroid of formula (II) and a method of use thereof are disclosed in U.S. Pat. No. 4,199,595 (1980) incorporated herein by way of reference.

Conveniently, the formula (I) acid may be prepared by the following route:

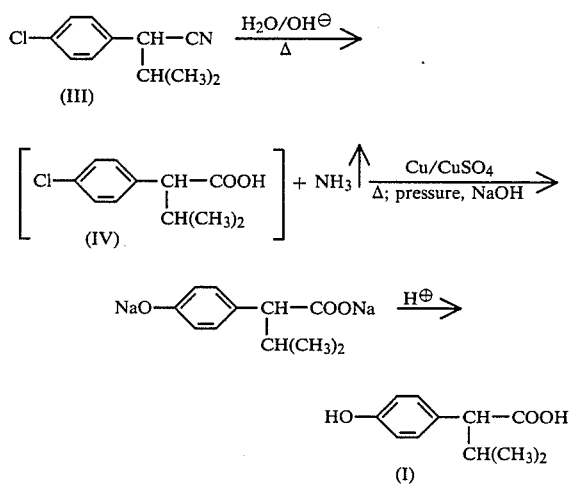

Thus, 2-(4-chlorophenyl)-3-methylbutyronitrile (III) is hydrolyzed with a concentrated alkali metal hydroxide selected from sodium or potassium hydroxide at elevated temperatures to the corresponding carboxylic acid formula (IV) with the concomitant evolution of ammonia gas. Next, the ring halogen of said acid (IV) is replaced with a hydroxyl group via a nucleophilic displacement reaction in the presence of a catalyst selected from a copper/cupric salt or a cupric salt (such as cupric chloride or sulfate and preferably cupric sulfate) at elevated temperatures and pressures in an alkaline medium to yield the desired acid of formula (I).

We find, that if said catalyst or catalyst mixtures are added to the reaction mixture at the very beginning of the above outlined sequence, then in the presence of same and especially under pressure, the ammonia gas generated may displace some of the chlorine atom attached to the ring. Unwanted aniline by-products may thus be formed, resulting in lower overall yields and/or less pure products.

We also find, that by the sequential, integrated, two-step process of the invention depicted above, and using only a cupric salt as catalyst, the desired product is obtained consistently in satisfactory yields and purity.

Consequently, the preferred process of the invention comprises: one molar equivalent of 2-(4-chlorophenyl)-3-methylbutyronitrile (III) is mixed with from about four to ten molar equivalents (preferably six molar equivalents) of about 50 to 80% by weight of aqueous sodium or potassium hydroxide (preferably 70% by weight of sodium or potassium hydroxide). The thus obtained mixture is stirred and heated from about 140° to 200° C. (preferably 150° to 160° C.) for about one to ten hours (preferably three to five hours) or until the nitrile hydrolysis is essentially complete. On completion of the hydrolysis, an approximately 30% aqueous solution of about two to 10 mol percent cupric sulfate catalyst is added, the reaction vessel is then sealed and heated at a temperature of about 190° to 250° C. (preferably 200° to 215° C.) and at a pressure of about 2 to 25 kg cm$^{-2}$ (preferably from about 4 to 12 kg cm$^{-2}$) for about one to 20 hours (preferably nine to 11 hours) or until the reaction is essentially complete. On completion of the reaction, the pressure vessel is cooled, vented, the catalyst removed from the reaction mixture by suitable means (i.e., by filtration), and the product recovered from the solution by conventional laboratory procedures (i.e., precipitation with a strong mineral acid such as sulfuric acid or hydrochloric acid).

The thus isolated acid of formula (I) is, usually, of sufficient purity to be used in the preparations described in U.S. Pat. No. 4,199,595, leading to the pyrethroid of formula (II); however, should it be desired, the acid (I) may be further purified (i.e., by recrystallization, reprecipitation, and the like).

The invention is further illustrated by the non-limiting examples set forth below.

EXAMPLE 1

Preparation of 2-(4-hydroxyphenyl)-3-methylbutyric acid by the process of the invention The starting material: 2-(4-chlorophenyl)-3-methylbutyronitrile (146.5 kg; 0.756 kg/mol), 50% aqueous sodium hydroxide (157.4 kg=78.7 kg real; 1.97 kg/mol) and anhydrous sodium hydroxide (103.4 kg; 2.584 kg/mol) are charged to an autoclave. The mixture is stirred and heated at about 155° to 160° C. for four hours, with the ammonia gas formed in the reaction being vented continuously. On completion of the hydrolysis, the copper sulfate catalyst solution (33.6 kg containing 9.5 kg CuSO$_4$.5H$_2$O; 0.0381 kg/mol) is added. The autoclave is then sealed. The reaction mixture is stirred and heated at 207° to 212° C. and a pressure of 4.9 to 5.6 kg cm$^{-2}$ for ten hours. The reaction mixture is then cooled to 95° C., diluted with water (284.4 kg), further cooled to 70° C. and filtered to remove the copper catalyst. The filtrate is adjusted to pH 2-3 with 50% sulfuric acid (454.5 kg=227.2 kg real; 2.319 kg/mol). The title product crystallizes out, and is filtered, washed and dried. By the above method and on the same scale, several preparations were run. The pertinent data are summarized in Table I below.

TABLE I

Preparation of 2-(4-hydroxyphenyl)-3-methylbutyric acid by the process of the invention on a 0.756 kg/mol scale

| Exp No | 2-(4-hydroxyphenyl)-3-methylbutyric acid | | | | | |
|---|---|---|---|---|---|---|
| | wet wt in kg | % wt loss on drying | dry wt in kg | % purity | wt of pure acid in kg | % yield |
| 1 | 180.92 | 24.7 | 136.23 | 95.0 | 129.41 | 89.7 |
| 2 | 208.18 | 32.9 | 139.69 | 93.0 | 129.91 | 90.1 |
| 3 | 188.64 | 28.1 | 135.63 | 96.0 | 130.23 | 90.3 |
| 4 | 216.82 | 36.0 | 138.76 | 93.5 | 129.73 | 90.0 |

What is claimed is:

1. A process for the preparation of 2-(4-hydroxyphenyl)-3-methylbutyric acid comprising: hydrolyzing 2-(4-chlorophenyl-3-methylbutyronitrile with a concentrated aqueous solution of an alkali metal hydroxide selected from 50 to 80% by weight of aqueous sodium or potassium hydroxide at a temperature from 140° to 200° C. for a period of time from one to ten hours or until the reaction is essentially complete, to the corresponding 2-(4-chlorophenyl)-3-methylbutyric acid, introducing into the reaction mixture an aqueous solution of 2 to 10 molar percent of a cupric salt selected from cupric chloride or cupric sulfate and displacing the halide with hydroxide at a temperature of 190° to 250° C. at a superatmospheric pressure of 2 to 25 kg cm$^{-2}$ for 1 to 20 hours, or until the reaction is essentially complete.

2. A process according to claim 1, wherein the base is 70% aqueous sodium hydroxide, the temperature of the hydrolysis is 150° to 160° C., the reaction time is three to five hours, the catalyst is three to five mol percent of cupric sulfate, the temperature range of displacing the halide with hydroxide is 200° to 215° C., and the pressure range of same is 4 to 6 kg cm$^{-2}$ and the reaction time is 9 to 11 hours.

* * * * *

TABLE II

Preparation of 2-(4-hydroxylphenyl)-3-methylbutyric acid, using a mixed cupric sulfate/copper catalyst

| Exp No | 2-(4-hydroxyphenyl)-3-methylbutyric acid | | | | | |
|---|---|---|---|---|---|---|
| | Reaction | | | | | |
| | temperature in °C. | pressure in kg cm$^{-2}$ | time in hrs | crude wt in g | % purity | pure wt in g | %* yield |
| 1 | 200 | 15.4–16.8 | 4 | 34.2 | 65.8 | 22.5 | 59.19 |
| 2 | 200 | 15.4–16.8 | 6 | 34.31 | 66.7 | 22.88 | 60.18 |
| 3 | 200 | 12.6 | 12 | 37.89 | 86.0 | 32.58 | 85.70 |
| 4 | 200 | 12.6 | 12 | 37.75 | 84.4 | 31.86 | 83.79 |

*The starting material is 98% pure, thus the % yield is adjusted accordingly.

EXAMPLE 2

Preparation of 2-(4-hydroxyphenyl)-3-methylbutyric acid

The starting material: 2-(4-chlorophenyl)-3-methylbutyronitrile (38.74 g; 0.2 mol), 50% aqueous sodium hydroxide (96.0 g=48.0 real; 1.2 mol), copper sulfate (2.5 g; CuSO$_4$.5H$_2$O; 0.01 mol) and copper dust (0.4 g; 0.007 mol) are mixed in a pressure vessel. The vessel is flushed with nitrogen and sealed. It is then heated at 200° C. and 15.4 kg cm$^{-2}$ pressure for four hours. The vessel is then cooled and vented. The reaction mixture is filtered and adjusted to 400 ml volume with water. The solution is adjusted to pH 1. The crystalline precipitate is filtered, washed, and dried under vacuum.

By the above procedure, several preparations are run. The pertinent data are summarized in Table II below.